United States Patent [19]
Delannoy

[11] Patent Number: 5,195,950
[45] Date of Patent: Mar. 23, 1993

[54] COMPRESSION BANDAGE WITH CALIBRATION MEANS

[75] Inventor: Robert Delannoy, Paris, France

[73] Assignee: Molinier SA, France

[21] Appl. No.: 804,957

[22] Filed: Dec. 11, 1991

[30] Foreign Application Priority Data

Dec. 11, 1990 [FR] France ............... 90 15877

[51] Int. Cl.5 ............... A61F 13/00; A61F 15/00
[52] U.S. Cl. ............................ 602/75; 602/76; 602/77
[58] Field of Search ............... 602/75, 76, 77; 73/760, 73/862.39

[56] References Cited

U.S. PATENT DOCUMENTS

| 3,613,679 | 10/1971 | Bijou ............................. 602/75 |
| 5,011,200 | 4/1991 | Glancy et al. ............. 73/862.39 |

FOREIGN PATENT DOCUMENTS 3640979 8/1987 Fed. Rep. of Germany ...... 128/169

*Primary Examiner*—Paul Prebilic
*Attorney, Agent, or Firm*—Eckert Seamans Cherin & Mellott

[57] ABSTRACT

The compression bandage with calibration means has visual marks (1) arranged according to a variable and gradually increasing distance (X), (X+1), (X+2), ... (X+n) in order to correspond to a decreasing pressure applied as and when the bandage is wrapped.

18 Claims, 2 Drawing Sheets

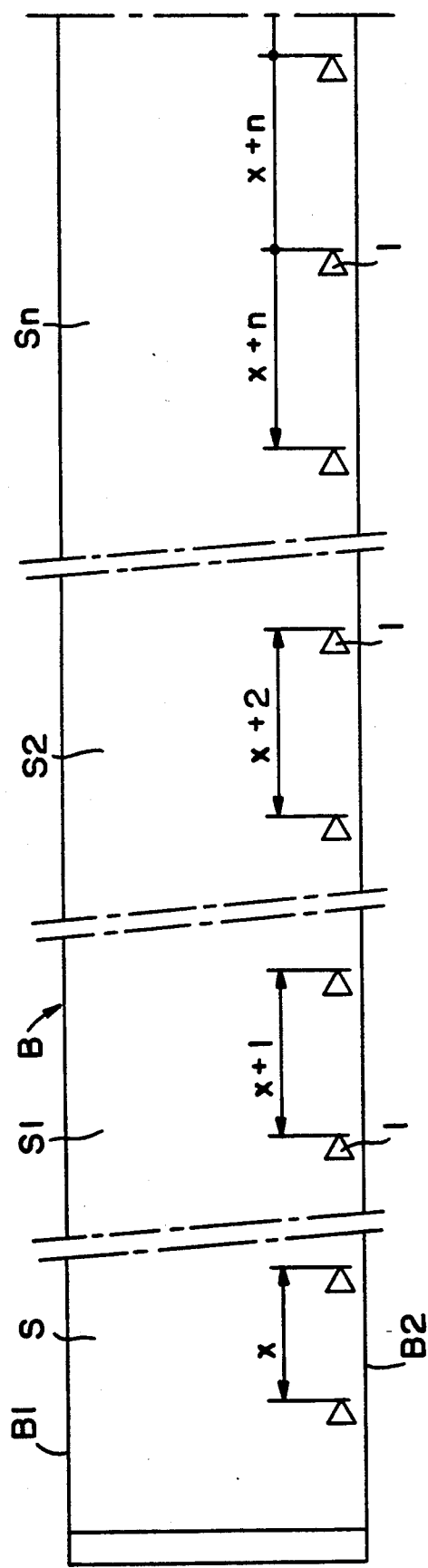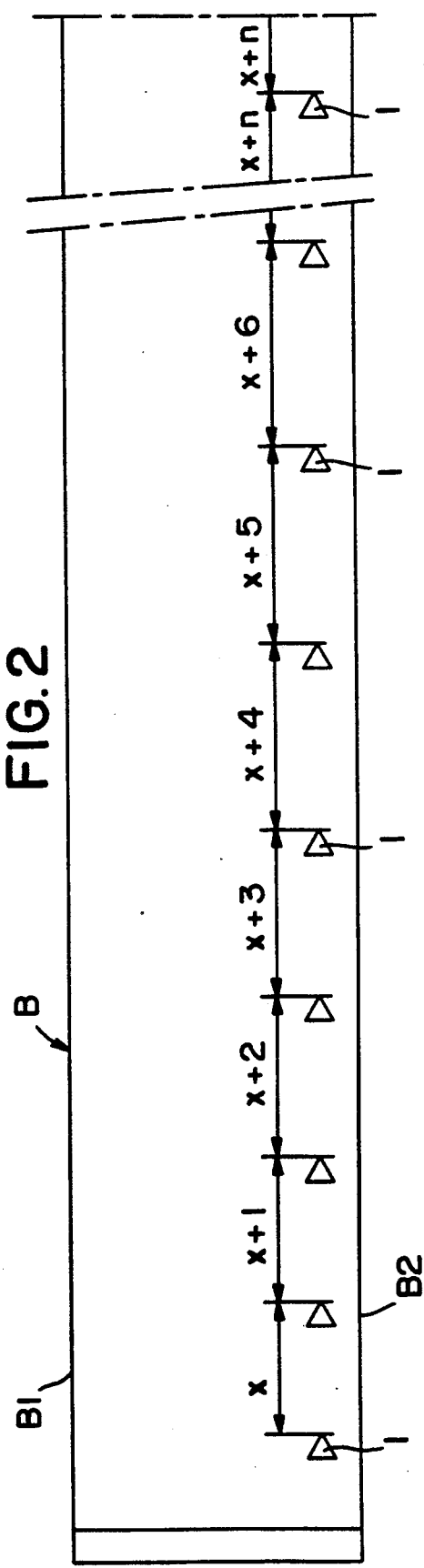

COMPRESSION BANDAGE WITH CALIBRATION MEANS

The invention most especially relates to compression bandages with a stretching capacity in the longitudinal direction and transversal direction, if required, designed to be wrapped, generally in helicoidal form, around a limb.

Depending on the pathological cases to be treated, it is very important to know the pressure applied by the bandage against the limb, as and when it is being wrapped, taking the elasticity of the said bandage into account.

In order to overcome this problem, compression bandages with calibration means for the user, are offered. As an example, this state of the art can be illustrated by the teaching of U.S. Pat. No. 3,613,679 and French patent 2 544 982. The U.S. Pat. No. 3,613,679 teaches a compression bandage whose central part, has marks of variable geometrical form evenly distributed over the whole length. The degree of elongation of the bandage and consequently, the resulting pressure applied against the limb, are measured visually by the deformation of the geometrical marks. The French patent 2 544 982 teaches an equivalent solution to that revealed in the American patent, i.e. the degree of elongation of the bandage is measured by the deformation of the marks on the said bandage. In a more specific manner, in the French patent 2 544 982, the problem is overcome by printing two parallel rows of dots, arranged at regular intervals on the middle part of the bandage. The two rows are separated by a distance greater than the interval separating two dots of the same row. When the bandage is stretched, the interval separating two dots, varies, thereby capable of reaching the length of the distance separating the two rows, which corresponds to a certain percentage of elongation. The German patent 2329372 is also known. This teaches a compression bandage with a device indicating the state of elongation of the bandage and indicates indirectly, the pressure applied. Furthermore, it is planned to equip the bandage with indicating devices which may be different in order for each of them to correspond to a certain degree of elongation. However, such indicating devices are arranged according to constant intervals so that it is only possible to obtain an indication at one particular point. Finally, it is necessary to highlight that it would be difficult to foresee the production of a compression bandage equipped in different areas with visual indications of different embodiments, on an industrial scale.

Therefore, it appears that although the solutions taught by any of these documents enable the degree of elongation of the bandage to be displayed, the pressure applied, according to the degree of elongation, is always constant. In fact, the visual marks, regardless of their geometrical forms, are separated by constant intervals throughout the length of the bandage.

However, it has been medically proven, particularly in phlebology, that the pressure applied by the bandage, from the foot going up to the thigh, must be decreasing, otherwise certain traumatisms may appear.

However, in order to clarify the invention, it is aimed at overcoming these disadvantages in a simple and efficient manner.

The problem the invention intends to solve is to be able to control and reduce the pressure applied by the bandage to the limb, as and when it is being wrapped.

This type of problem is overcome in that the bandage has visual marks, arranged according to a variable and gradually increasing distance in order to correspond to a pressure applied decreasingly, as and when the bandage is wrapped.

In order to overcome the problem brought up to arrange the visual marks according to a variable and gradual distance, different solutions can be examined. In one embodiment, the marks are arranged according to several series. For each series, the said marks are spaced at a different pitch, the pitch of each of these series gradually increasing. In another embodiment, the marks are arranged according to a variable and gradually increasing distance, continuously.

In an advantageous manner, considering the problem brought up, the marks are arranged on the bandage by a jet of ink, however, not to the exclusion of any other technique enabling a similar result to be obtained.

The marks are arranged in line according to the direction of elongation of the bandage and parallel to the selvedges.

Another problem the invention intends to solve, is to make the marks invisible as and when the bandage is wrapped. In known techniques, such as those aforementioned, after positioning the compression bandage on the limb, the calibration marks are visible which is not very attractive. This kind of problem is overcome in that the marks are arranged along the selvedge or close to one of the selvedges.

According to another characteristic, the marks are of any geometrical form. It is to be noted that these geometrical forms may indicate the wrapping direction of the bandage.

The invention is now described in more detail with the said of the attached drawings, wherein:

FIG. 1 is a plan view of the bandage according to a first embodiment,

FIG. 2 is a similar view to FIG. 1, showing another embodiment of the bandage,

The compression bandage, according to the invention, is of any known and suitable type, resulting from the interlacing of warp and weft threads, woven or knitted, of type and texture determined to provide the bandage with a certain degree of elasticity, particularly longitudinally. This bandage is generally referred to as (B).

According to another characteristic based on the invention, the bandage (B) has visual marks (1) arranged according to a variable and gradually increasing distance. In the embodiment illustrated in FIG. 1, marks (1) are arranged according to several series (S), (S1), (S2), ... (Sn) each comprising a certain number of marks. For each series, the marks (1) are spaced at a different pitch, the pitches of each of these series, increasing. For example, if the marks of the first series (S) are spaced by a pitch (X), those of the second series (S1) are spaced by a pitch (X+1), those of the third series (S2), by a pitch (X+2) and so on, up to the end of the bandage where the marks of the last series (Sn) are spaced by a pitch (X+n).

In the embodiment illustrated in FIG. 2, marks (1) are arranged between each end of the bandage, according to a variable distance (X), (X+1), (X+2), (X+n) and gradually increasing, continuously.

The different marks (1) are arranged in the conditions aforementioned, i.e. according a variable and gradually increasing distance, therefore being aligned in the direction of the elongation of the bandage, parallel to the selvedges (B1) (B2).

Considering these arrangements, it is possible to control the pressure applied by the bandage (B) to the limb, as and when it is wrapped. In a particularly advantageous manner, it appears that the pressure applied decreases, as and when the bandage is wrapped, resulting in the variable and gradually increasing distance of the visual calibration marks (1). For example, if, when wrapping the bandage around the limb, it is stretched so that after extension, the marks correspond to the length of the thumb (PO), it can be seen, that as and when the bandage is wrapped, it is stretched by a lesser value, so that the distance between two marks always corresponds to the length of the thumb (PO) which is invariable, thereby making up the basis of the calibration. Obviously, the gauge length represented by the thumb, is given for guidance only and is not limited as it is obviously possible to use any measuring means.

Figure 3:
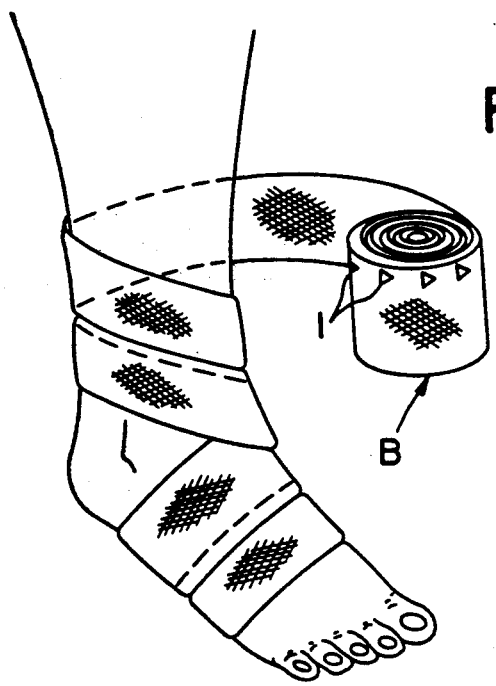
FIG. 3 is a perspective view showing the wrapping of the compression bandage according to the invention on the lower limb.
Figure 4:
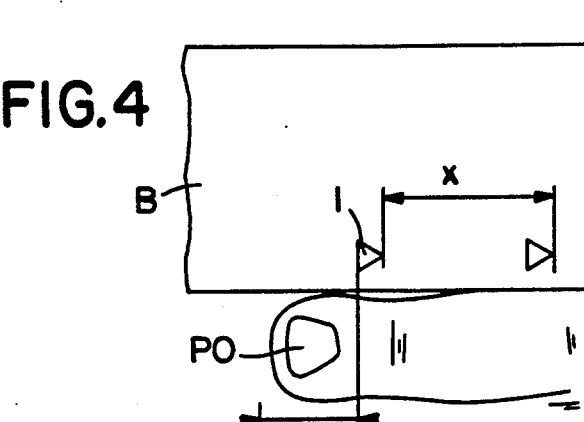
FIGS. 4, 5, 6 and 7 are purely schematic views showing the calibration principle, according to the invention and the reduction of the pressure applied, as and when the bandage is wrapped.
Figure 5:
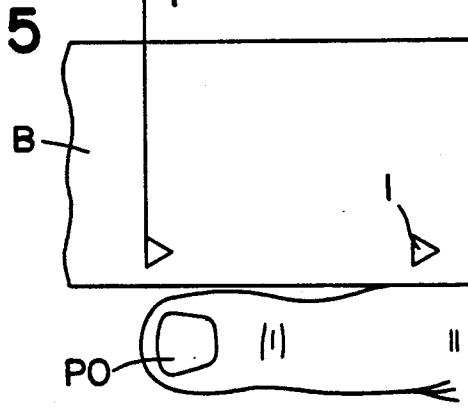
Figure 6:
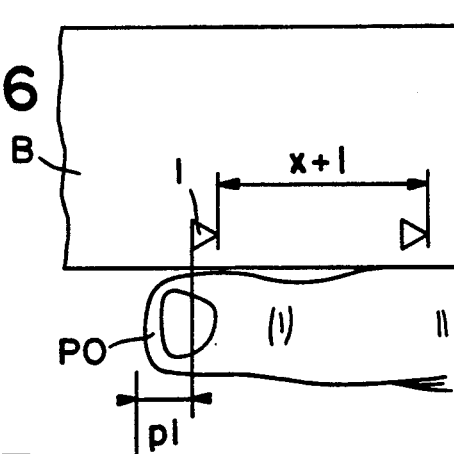
Figure 7:
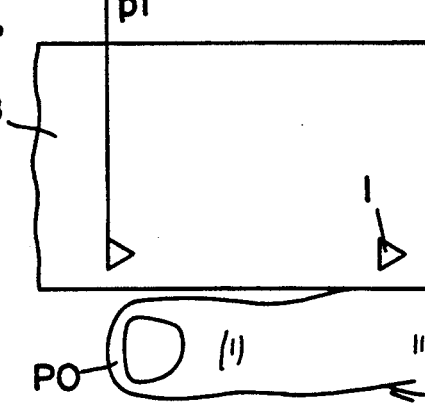

FIGS. 4, 5, 6 and 7 are purely schematic views illustrating the control and tension principle of the bandage according to the invention. FIG. 4 shows part of the bandage at the end of wrapping, where, for example, the marks (1) are separated by an interval (X). The thumb (PO) of the user has been illustrated in front of these marks. At this stage, the bandage is represented in the relaxed condition, i.e. before elongation. FIG. 5 is a view corresponding to FIG. 4, showing the elongation of the bandage, in order to arrange the marks (1) according to the length of the thumb (PO). By comparing these two figures, it can be seen that is was necessary to elongate the bandage, according to a value (P) corresponding to a certain degree of pressure. FIG. 6 shows another part of the bandage where the marks (1) are separated by an interval (X +1). In the same way as previously shown, the thumb (PO) of the user has been represented in front of these marks. The bandage is represented before elongation. FIG. 7 shows the bandage is stretched in order to arrange the marks (1) according to the length of the thumb (PO). If FIGS. 6 and 7 are compared as previously, it can be seen that it was necessary to elongate, in this case, the bandage according to a pressure (Pl), less than pressure (P).

Another problem the invention intends to solve is to make the different marks (1) invisible as and when the bandage is wrapped. With this in mind, marks (1) are arranged along the selvedge or close to one of the selvedges (B1) (B2) of the bandage. Given these conditions, considering the helicoidal type wrapping of the bandage and partial overlapping of the different coils, it appears that the marks are automatically hidden by the parts covered by the bandage.

In an advantageous manner, the different marks (1) are obtained by the known ink jet technique, by any suitable means, enabling these marks to be positioned with a variable and gradually increasing distance. Once again, this printing technique by ink jet only represents a preferred embodiment, since the marks can be inscribed on the bandage by any technique enabling similar results to be obtained.

In the figures of the drawings, the marks illustrated are of a triangular geometrical shape, not to the exclusion of other geometrical shapes. These geometrical shapes may, advantageously, indicate the wrapping direction of the bandage.

The advantages are made well apparent from the description and the following is highlighted and reminded in particular :

the possibility of controlling the pressure applied by the bandage against the limb, whilst enabling this pressure to be reduced, as and when it is wrapped, the simple manufacture, the invisibility of the calibration marks, after the bandage has been wrapped.

I claim:

1. Compression bandage with calibration means, comprising a plurality of visual marks spaced along a length of the bandage at a variable and gradually increasing distance between said marks, the bandage being stretchable and having constant elasticity along the length, whereby when the bandage is stretched around a body part, a uniform distance between said marks indicates a gradually decreasing pressure on the body part along the length of the bandage.

2. Bandage according to claim 1, wherein the plurality of marks are arranged according to several series, and wherein for each of the series said marks are spaced at different distances, the distances between the marks in each of the series being gradually increased along said length.

3. Bandage according to claim 1, wherein the marks (1) are arranged according to a variable and gradually increasing distance (X),(X+1), (X+2)..., (X+n), continuously.

4. Bandage according to claim 1, wherein the marks are ink jet printed marks.

5. Bandage according to claim 1, wherein the marks are aligned in a direction of elongation of the bandage and parallel to selvedges of the bandage.

6. Bandage according to claim 5, wherein the marks (1) are arranged along the selvedge or close to one of the selvedges (B1).

7. Bandage according to claim 1, wherein the marks (1) are of any geometrical form.

8. Bandage according to claim 2, wherein the marks are ink jet printed marks.

9. Bandage according to claim 3, wherein the marks are ink jet printed marks.

10. Bandage according to claim 4, wherein the marks are aligned in a direction of elongation of the bandage and parallel to selvedges of the bandage.

11. Bandage according to claim 8, wherein the marks are aligned in a direction of elongation of the bandage and parallel to selvedges of the bandage.

12. Bandage according to claim 9, wherein the marks are aligned in a direction of elongation of the bandage and parallel to selvedges of the bandage.

13. Bandage according to the claim 10, wherein the marks (1) are arranged along the selvedge or close to one of the selvedges (B1).

14. Bandage according to claim 11, wherein the marks are arranged along the selvedge or close to one of the selvedges (B1).

15. Bandage according to claim 12, wherein the marks are arranged along the selvedge or close to one of the selvedges (B1).

16. Bandage according to claim 13, wherein the marks (1) are of any geometrical form.

17. Bandage according to claim 14, wherein the marks (1) are of any geometrical form.

18. Bandage according to claim 15, wherein the marks (1) are of any geometrical form.

* * * * *